United States Patent [19]
Flammang et al.

[11] Patent Number: 5,172,694
[45] Date of Patent: Dec. 22, 1992

[54] SINGLE PACING LEAD AND METHOD UTILIZING TWO DIFFERENT FLOATING BIPOLES

[75] Inventors: Daniel Flammang, Angouleme, France; Frits M. van Krieken, Dieren, Netherlands

[73] Assignee: Vitatron Medical B.V., Dieren, Netherlands

[21] Appl. No.: 707,444

[22] Filed: May 30, 1991

[51] Int. Cl.$^5$ .............................................. A61B 5/046
[52] U.S. Cl. .................................... 128/642; 128/785; 128/419 P; 128/696
[58] Field of Search ........ 128/419 D, 419 P, 419 PG, 128/642, 696, 700, 784–786

[56] References Cited

U.S. PATENT DOCUMENTS 3,903,897  9/1975  Woollons et al. .............. 128/642 X
4,962,767  10/1990  Brownlee ..................... 128/696 X

OTHER PUBLICATIONS

Goldreyer et al., "A New Orthogonal Lead For P-Synchronous Pacing", *PACE*, 1981, 4:638–644.
Goldreyer et al., "Orthogonal Electrogram Sensing", *PACE*, 1983, 6:464–469.
Brownlee, "Toward Optomizing the Detection of Atrial Depolarization With Floating Bipolar Electrodes", *PACE*, 1989, 12:431–442.

*Primary Examiner*—Lee S. Cohen
*Assistant Examiner*—Brian L. Casler
*Attorney, Agent, or Firm*—Woodcock Washburn Kurtz Mackiewicz & Norris

[57] ABSTRACT

There is provided a pacemaker lead for use in a dual chamber pacemaker system, wherein the single lead provides for ventricular pacing and atrial sensing. The lead has at least two floating bipoles positioned for placement in the atrium. A first whole-ring bipole is positioned a distance from the distal end so as to be positioned in the lower atrium of an average patient when the distal end is in position for ventricular pacing, and a second split-ring bipole is placed on the lead proximal from the first bipole so as to be positioned in the upper atrium of the normal patient. The method thus comprises positioning a floating whole-ring bipole in the lower atrium, and/or positioning a floating split-ring bipole in the upper atrium. The pair of bipoles so placed provide for atrial sensing with a high degree of ventricular far-field rejection, enabling VDD pacing and also monitoring of P-wave direction and conduction duration.

13 Claims, 2 Drawing Sheets

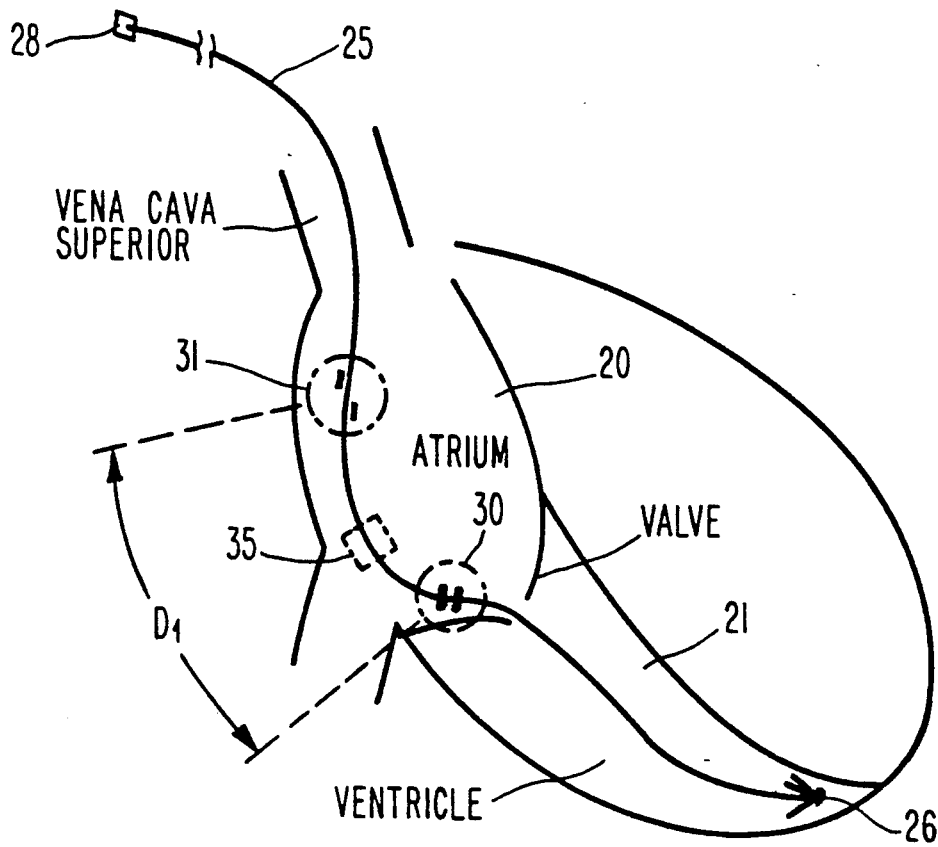
Fig. 1
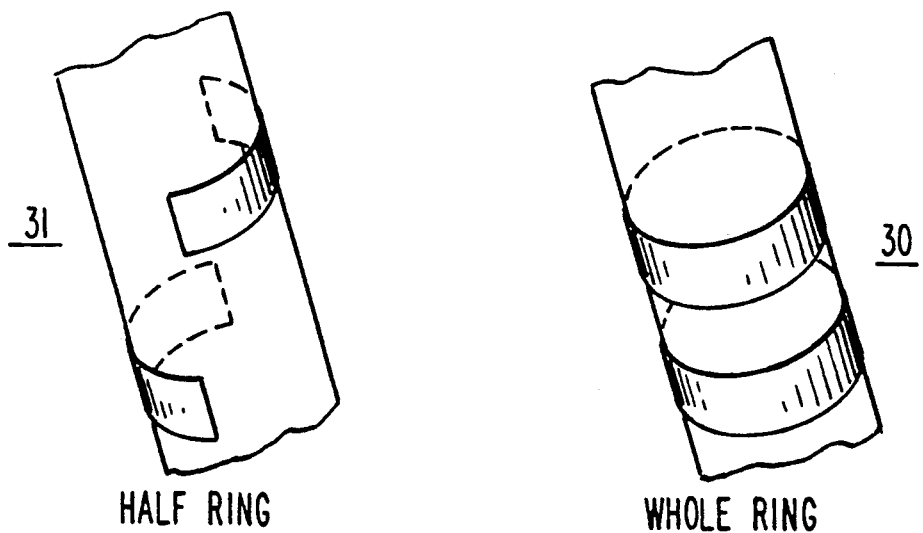
HALF RING
Fig. 1B
WHOLE RING
Fig. 1A

SINGLE PACING LEAD AND METHOD UTILIZING TWO DIFFERENT FLOATING BIPOLES

BACKGROUND OF THE INVENTION

This invention relates to leads for use with dual chamber pacemakers and, more particularly, to a single lead system and method of using same for providing at least ventricular stimulation and also providing atrial sensing through two spaced floating bipoles located on the lead.

Dual chamber pacemakers are recognized to have a greater capacity for optimum physiologic stimulation of the heart than single chamber devices, for many patients. However, dual chamber systems conventionally require implantation of two intracardiac leads, which has long been widely viewed as an obstacle. A dual chamber system using a single multipolar lead to sense the atrium and to stimulate the right ventricle, i.e., operating in a VDD mode, can avoid the difficulties related to separate atrial lead implantation. Such VDD stimulation using a single lead for atrial sensing and ventricular pacing has become a reality. During the last decade, several such systems for permanent atrial sensing and pacing have been tested. More recently, new types of multipolar leads have been developed using novel arrangements where electrodes are positioned on the atrial floating portion of a single right ventricular catheter. See, for example, the paper of Goldreyer et al., "A New Orthogonal Lead For P-Synchronous Pacing," PACE, 1981, 4:638-644; Goldreyer et al., "Orthogonal Electrogram Sensing," PACE, 1983, 6:464-469; Brownlee, "Toward Optimizing the Detection of Atrial Depolarization With Floating Bipolar Electrodes," PACE, 1989, 12:431-442.

At the present time, a half-ring electrode system is commercially available. This system consists of a unipolar VDD pacemaker and a single lead with a ventricular pacing electrode and a single supplementary half-ring bipole on its proximal atrial floating portion. Also, pacemakers have been introduced with Holter capabilities for monitoring and storing cardiac rhythm abnormalities, although these capabilities are generally limited to certain simple arrhythmias. Thus, the detection of the atrial electrogram (AEG) and the technical means for Holter monitoring and storage, are generally known in the prior art.

However, these systems have not proven reliable with respect to several crucial variables. For example, any reliable VDD system needs to provide an AEG with an acceptable minimum level. Also, it is important that atrial sensing have a high ventricular far-field rejection. As used herein ventricular far-field rejection is calculated by dividing the mean atrial electrogram amplitude, AEG, by the corresponding mean ventricular electrogram amplitude (VEG). Also, it is desirable to have means for obtaining more diagnostic information, including reliable means for measuring the intra-atrial P-Wave direction and conduction time, and recording same. Also, it would be desirable to have a single lead system with which the atrium could also be paced, thereby providing dual chamber pacing capability.

SUMMARY OF THE INVENTION

The invention provides a reliable system and method for VDD pacing. Specifically, there is provided a single dual chamber lead for providing reliable ventricular pacing and atrial sensing from at least two atrial locations, with a high ventricular far-field rejection in atrial sensing. By reliably sensing at two different atrial locations, the pacing system can also determine P-wave direction and conduction time, for dispositive and system control purposes.

The single lead of this invention suitably comprises a first whole-ring bipole positioned at a distance from the distal end so as to be positioned in the lower atrium of a patient when the distal end is in proper position for ventricular pacing, and a second split-ring bipole separated proximally from the first bipole so as to be positioned in the upper atrium of a patient. The electrodes of the two bipoles are suitably about 10 mm$^2$ in surface area. The electrodes of the split-ring bipole are preferably displaced diagonally or orthogonally. The two bipoles are generally positioned at a distance of about 15-60 mm between their centers, to provide the desired spacing. In another embodiment adapted to work for different size persons, the two bipoles are positioned closely together on the lead surface to provide substantially mid-atrial placement in the patient, with the whole-ring bipole being proximal to the split-ring bipole so as to provide the choice of the whole-ring bipole if the pair of bipoles is positioned near the tricuspid valve and the choice of the split-ring electrode if the pair of bipoles is positioned near the sinus node.

BRIEF DESCRIPTION OF THE DRAWINGS

FIG. 1 is a schematic representation of a single lead of this invention placed in a patient's heart showing a whole-ring bipole placed in the lower atrium and a split-ring bipole placed in the upper atrium. FIG. 1A is an enlarged view of a typical whole-ring electrode; FIG. 1B is an enlarged view of a half-ring bipole, with diagonal displacement.

DESCRIPTION OF THE PREFERRED EMBODIMENTS

Figure 2:
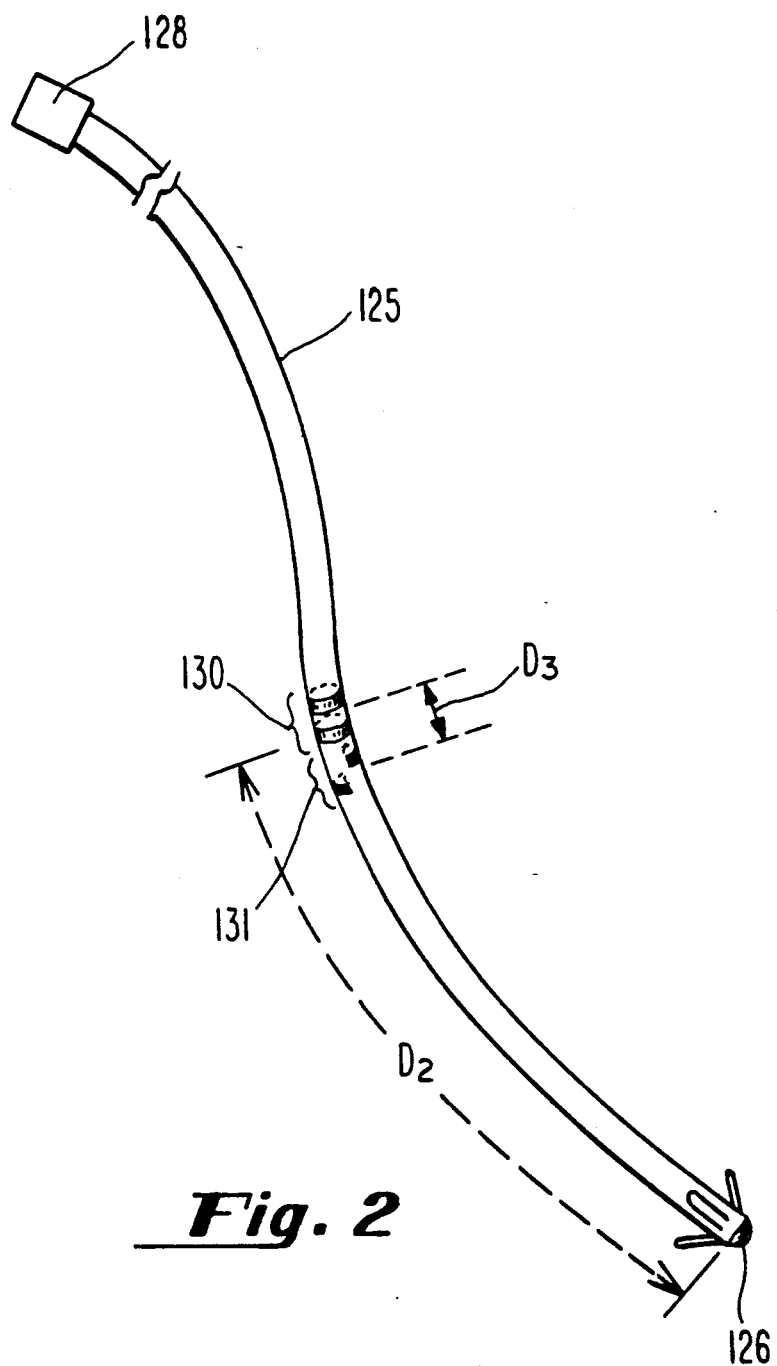
FIG. 2 is a schematic representation of a single lead having a pair of bipoles spaced closely together, the pair having a split ring bipole which is distal to a whole-ring bipole.

Referring now to FIG. 1, there is shown a diagrammatic representation of a lead 25 in accordance with this invention, positioned in a patient's heart. The lead has a pacing electrode 26 positioned at the distal end thereof. FIG. 1 illustrates a unipolar pacing electrode 26, and in a pacemaker system the other electrode is the case or portion of the case of the pacemaker itself, as is well known in the art. Alternately, there may be provided a pair of electrodes at about the tip end, providing for bipolar pacing, as well as detecting, in the ventricle. As is well known in the art, the lead is positioned in the right ventricle for good contact with the heart wall, and the lead may include tines or other anchoring means for holding the pacing lead in position.

As illustrated, when the distal portion of the lead is positioned in the ventricle 21, a proximal portion is positioned in the atrium 20. The proximal end of the lead has a connector 28 shown schematically, for connection to a pacemaker 129. Alternately, if the lead is used with an external pacemaker or analyzer device, connector 28 may be plugged into any suitable mating connector means for receiving the lead. As is common in the art, a conducting wire or wires extend the length of the lead for electrically connecting the distal electrode or electrodes to the connector, whereby stimulus pulses may be transferred through to the distal end and signals sensed in the ventricle may be transmitted back to the pacemaker or other receiving instrument.

In the invention as shown, the floating portion of the lead which passes through the atrium has a pair of bipoles 30, 31, illustrated in FIGS. 1A and 1B. As used herein, the term "bipole" refers to a pair of electrodes. In this case, the lead 25 is floating in the atrial region, i.e., it is not pressed against the atrial wall, except by chance, such that bipoles 30, 31 are floating relative to the chamber walls. Bipole 30, which is in the lower portion of the atrium near the tricuspid valve (between the atrium and the ventricle) is a whole-ring electrode, as shown in FIG. 1A. The whole-ring bipole is suitably a conventional arrangement of electrode rings which circle the outer circumference of the generally cylindrical lead 25. Typically the surface area of each ring of the whole-ring bipole 30 is about 10 mm$^2$, but preferably greater than 5 mm$^2$. It has been found that it is important, also, that the areas of the respective electrodes are balanced, i.e., about equal. While the term "whole-ring" generally refers to rings which encompass all 360° of the lead circumference, as used in the claims defining this invention "whole-ring" refers to any ring which circles at least 75% of the circumference. As illustrated in FIG. 1, the whole-ring bipole is floating, i.e., there is no mechanism for anchoring the bipole against the atrial wall.

The other bipole, illustrated at 31, is a split-ring bipole, and in its preferred embodiment as illustrated in FIG. 1B is a half-ring bipole, with the half-rings diagonally oriented. Although illustrated as a half-ring bipole in FIG. 1B, in this invention bipole 31 is generally a split-ring bipole, meaning that each separate electrode extends less than 75% of the distance around the circumference of the lead. The electrodes of each split-ring pair have the same surface area, i.e., about 5 to 10 mm$^2$. Preferably, for the practice of this invention, the split-ring bipole 31 is also diagonal, meaning that the two electrodes are rotated circumferentially between about 90° and 270° relative to each other around the longitudinal axis of lead 25. Further, such split-ring electrodes may be substantially orthogonal, as that term is used in the art literature. However, as used herein, the term "split-ring" does not require that the rings also be diagonal. Each bipole has a pair of wires (not shown) connecting to connector 28.

In practice, a physician positions the lead so that the distal electrode 26 is positioned in the ventricle for good ventricular pacing. Bipole 30 is positioned sufficiently proximal, i.e., about 90–110 cm from the distal tip, so that it lies within the atrium, although within the lower atrium near the tricuspid valve. It is our observation that in this position, the whole-ring bipole provides the best performance in terms of sensing the P-wave and rejecting the far field ventricular QRS signal. At the same time, the split-ring bipole 31 provides a better performance in the upper atrial position in terms of sensing the P-wave and rejecting the far field QRS.

In practice, the distance D between the upper atrial and lower atrial bipoles is established to optimize sensing of the P-wave timing and direction. A particular use of the atrial lead of this invention is to obtain separate sensings of P-waves at different locations to determine the direction of atrial depolarization, i.e., to determine whether the P-wave is antegrade or retrograde. For this purpose, the bipole separation $D_1$ is suitably in the range of about 15 to 60 mm.

FIG. 2 is a schematic representation of another lead 125 which utilizes the general principles discussed above. The purpose of the lead design of FIG. 2 is to provide a single lead of uniform construction which provides a floating bipole suitable for atrial sensing in different patients having a range of heart sizes. A very common problem for pacing systems utilizing a single floating bipole for sensing in the atrium is that the one bipole must be implanted in a carefully selected atrial position, whereas the heart size may vary considerably from patient to patient. This is frequently difficult to achieve because the distal tip must be carefully fixed for good ventricular pacing. Recognizing that the optimum choice between split-ring and whole-ring, or diagonal-ring bipole, is a function of the position within the atrium, and recognizing that there is a range of variation in heart size, a manufacturer would need to produce a wide variety of leads for selection by the physician in order to optimize conditions for any given patient. For example, a pacemaker company may sell leads with different lengths between the ventricular tip and the atrial bipole, but even then the physician would be required to carefully position the bipole in the atrium, a task which is made difficult by the need to position the distal tip properly in the ventricle for pacing purposes.

The lead of FIG. 2 provides a single-dimension lead with a great degree of latitude for the physician. Lead 125 has a pair of bipoles 130, 131 positioned at a distance $D_2$ proximal from the electrode 126, which is located at about the distal tip. The distance $D_2$ is selected to be approximately in a mid-atrial position for most patients when the electrode 126 is properly located for ventricular pacing. In this configuration, bipole 130, which is the whole-ring bipole, is shown positioned proximal to the split-ring bipole 131. Although this arrangement is preferable, the relative positions can be reversed. The two bipoles are positioned relatively closely together, i.e., having their mid-points separated by a distance $D_3$ which is preferably about 7 mm and within a range of about 5–10 mm. Each bipole has wires connecting to a connector 128; electrode 126 also is connected by a wire through the lead to connector 128.

When the lead is implanted and electrode 126 is properly positioned, the physician determines which bipole to utilize. If, due to the size of the patient heart, the bipoles are positioned in the high atrium, the split-ring bipole 131 is selected, for the reasons stated above. Note that in order to minimize the risk that the split-ring bipole is proximal to the sinus node, i.e., out of the atrium, it is preferable to have the split-ring electrodes positioned as the distal bipole of the pair. Conversely, in a circumstance where the bipole pair 130, 131 is positioned in the lower atrium near the tricuspid valve, the fact that whole-ring bipole 130 is positioned as the proximal bipole of the pair helps ensure that it lies within the atrium. Thus, there is provided a standard lead having a pair of bipoles, either one of which may be selected depending upon whether the pair is positioned in the high or low atrium.

In practice, the lead of FIG. 2 may be constructed such that each of the respective bipoles has its own pair of conductors (wires) and its own connector. In such case, after selecting the optimum bipole, the connector associated with the non-selected bipole may be removed by the physician, the selected connector then being used to plug into the pacemaker or other receiving circuit in a conventional manner. In another embodiment, all four conductors associated with the two bipoles can be brought out to one connector, along with the conductor from electrode 126, and a coupling (matching) connector piece (not shown) utilized to couple only the pair of conductors associated with the selected bipole to the pacemaker. Alternately, one pair of conductors may be utilized, with electronically-activated switching means utilized to connect the distal end of the conductor pair to the selected bipole. It is to be noted that the lead of this invention, as claimed, does not depend upon the specific arrangement for connecting the selected bipole through to the proximal connector. Also, due to a possible secondary displacement of the atrial portion of the lead, the pacemaker may be adapted to automatically select, at any time, the atrial bipole providing the largest AEG.

In another embodiment, the lead of FIG. 1 may be modified to provide an additional bipole at the position indicated by the dashed block at 35 in FIG. 1. Thus, the basic arrangements of FIG. 1 and FIG. 2 may be combined, adding the bipole pair of FIG. 2 placed substantially centrally between bipoles 30 and 31. In general, any number of additional bipoles or selectable bipole pairs may be added to the lead between bipoles 30 and 31, with appropriate selecting means for selecting which additional bipole or bipoles are utilized and conducting means for conducting sense signals through to connector 28. Additional such bipoles may be desirable in certain applications for providing more data useful in tracking the timing and direction of P-waves within the atrium.

We have conducted tests using four different leads. A first lead used a quadripolar orthogonal electrode system, as per Goldreyer. The orthogonal bipoles were positioned 90 mm and 130 mm respectively from the distal tip. Each electrode of the bipole had a surface area of about 1.5 mm². A second experimental lead comprised whole-ring bipoles positioned at 96 mm and 135 mm from the distal tip. The bipoles had a center-to-center separation of about 5 mm and each electrode had a surface of 9.8 mm² Another experimental lead had bipoles at the same distances and had the same electrode surface areas, but the bipoles were half-ring diagonal. A fourth lead is a commercially available lead, termed CCS, having only one half-ring bipole 136 mm from the distal tip. The electrodes of this bipole had surface areas of 7.85 mm² and an 8 mm separation.

The first experimental lead using a quadripolar orthogonal system was tested in a first group of 36 patients. The second and third experimental leads were used in a second group of 17 patients. The patients were randomized into two groups: the whole-ring system was tested in 7 patients, and the half-ring system in 10 patients. The fourth lead was used in the same group of 17 patients; in 10 of them it was compared to the experimental half-ring lead; in the other 7 patients, it was compared to the experimental whole-ring lead. The results of the test are presented in the following table:

|  | Ortho | Half-Ring | Whole-Ring | CCS |
| --- | --- | --- | --- | --- |
| Atrial Electrogram Amplitude | | | | |
| Prox Min | 0.74 ± 0.13 | 1.53 ± 0.32 | 0.88 ± 0.38 | 1.27 ± 0.18 |
| Prox Max | 1.61 ± 0.24 | 2.79 ± 0.62 | 1.94 ± 0.95 | 2.10 ± 0.25 |
| Distal Min | 0.30 ± 0.06 | 0.74 ± 0.27 | 1.22 ± 0.43 | |
| Distal Max | 8.55 ± .011 | 1.47 ± 0.46 | 2.00 ± 0.70 | |
| Ventricular Electrogram Amplitude | | | | |
| Prox Min | 0.11 ± 0.01 | 0.06 ± 0.01 | 0.07 ± 0.01 | 0.14 ± 0.03 |
| Prox Max | 0.12 ± 0.02 | 0.06 ± 0.01 | 0.06 ± 0.01 | 0.14 ± 0.03 |
| Distal Min | 0.19 ± 0.04 | 0.17 ± 0.06 | 0.07 ± 0.01 | |
| Distal Max | 0.24 ± 0.05 | 0.17 ± 0.06 | 0.07 ± 0.01 | |
| Ventricular Far Field Rejection | | | | |
| Prox Min | 7.8 ± 1.5 | 29.6 ± 7.0 | 15.0 ± 7.6 | 14.4 ± 3.0 |
| Prox Max | 19.1 ± 4.3 | 53.9 ± 12.8 | 33.8 ± 19.1 | 22.9 ± 3.7 |
| Distal Min | 2.7 ± 0.7 | 6.0 ± 2.8 | 17.1 ± 7.1 | |
| Distal Max | 5.4 ± 1.3 | 12.5 ± 5.0 | 27.8 ± 10.4 | |

The above data is to be reviewed from the concept of a safe arrhythmia diagnostic and VDD stimulating system, the most critical signals being the lowest AEG amplitude and the highest value of ventricular far-field rejection. In this regard, the comparison between the whole-ring and half-ring system shows that the half-ring system provided the best AEG amplitudes and ventricular far-field rejection at the proximal level. However, at the distal level, it was the whole-ring system that provided the best results, with the highest AEG amplitude and the largest ventricular far-field rejection. There is thus indicated the unique o combination presented by the lead of FIG. 1 as described above, having a floating whole-ring bipole positioned at the distal or lower atrial location and a floating split-ring electrode positioned at the proximal, or upper atrial location. It is also observed that the interelectrode distance of 5 mm, as used in the experimental leads, is preferable to the 8 mm in the CCS system. Also, the surface electrode size of up to about 10 mm², and the close balancing or equating of surface areas of electrodes in a pair, are important.

In testing the experimental leads, we also measured interatrial P-wave direction and calculated conduction time. The lead of FIG. 1 provided very high specificity and sensitivity. Retrograde V-A conduction was observed during ventricular pacing, and the morphology and the polarity of the interatrial depolarizations during ventricular pacing were quite different than that recorded in sinus rhythm. The lead of FIG. 1 is well suited for providing reliable information for recording AEG amplitudes and morphology. This information, associated with information from ventricular sensing, can be used in pacemaker systems for rhythm analysis and Holter monitoring, providing the capability for selecting the most appropriate mode of stimulation. Thus, with the single multi-polar lead of this invention, reliable atrial electrograms can be detected by tiered floating bipoles, and P-wave direction and conduction time can be measured from AEGs recorded at two distinct atrial levels. Through an appropriate algorithm, a beat-to-beat comparison with o sinus rhythm features allows analysis of rhythm disturbances, which analysis can be stored and/or displayed in a Holter system, and can provide an accurate tool useful for patients' treatment and for improved physiologic cardiac stimulation.

During our tests with the experimental leads, we also successfully achieved atrial stimulation through the -proximal bipole. The voltage threshold of the stimulation was quite satisfactory, indicating that an upper atrial bipole of the lead of this invention may also provide for dual chamber pacing.

The preferred embodiments of the single lead as described in the specification are useful in combination with available pacemakers for providing dual chamber pacemaker systems. The pacemaker may have any range of programmable means for switching modes of operation, within the scope of this invention.

The novel lead of this invention may also be used together with a conventional J-type atrial lead positioned in the atrial appendix, having an electrode touching the heart muscle. Although such an arrangement would have the detriment of requiring implantation of the second lead, such a classical dual lead DDD or DDDR system would be enhanced by having at least one extra diagnostic bipole. For example, the lead carrying the ventricular pacing tip may have a single floating bipole, suitably whole-ring, positioned in the lower atrium, with no second bipole for the upper atrium. With such an arrangement atrial sensing can be accomplished between the floating bipole and the bipole positioned in the atrial appendix. The atrial appendix bipole, since it touches the heart muscle, provides a greater mV signal, and as well provides the other advantages that go with the conventional two-lead arrangement.

What is claimed:

1. A lead for use with a pacemaker, said lead having at about its proximal end a connector for connecting to said pacemaker, a stimulus electrode at about its distal end for delivering stimulus signals, at lest two bipoles positioned for sensing signals in said atrium, and conducting means for conducting signals between said electrode and said connector and between said bipoles and said connector, characterized by:
    a first bipole positioned a distance from said distal end so as to be positioned in the lower atrium of an average patient when said distal end is in position for ventricular placing and a second bipole positioned proximal from said first bipole so as to be positioned in the upper atrium of a normal patient, and wherein said first bipole comprises a pair of whole-ring electrode and said second bipole comprises a pair of split-ring electrode.

2. The lead as described in claim 1, wherein said second bipole comprises half-rings.

3. The lead as described in claim 1, wherein the electrodes of each said bipole have surface areas in the range of about 5-10 mm$^2$.

4. The lead as described in claim 1, wherein for each said bipole the electrodes have balanced surfaces areas.

5. The lead as described in claim 1, wherein said split-rings are positioned substantially diagonally.

6. The lead as described in claim 1, wherein said first bipole positioned about 90 to 110 mm for said distal end and the surface areas of the electrodes of said first bipole are substantially balanced and in the range of 5-10 mm$^2$.

7. The lead as described in claim 1, wherein said second bipole is positioned about 15 to 60 mm proximal from said first bipole.

8. The lead as described in claim 1, further comprising a split-ring bipole and a whole ring bipole positioned intermediate of said first and second bipoles.

9. A method of positioning bipole electrodes in a patient's atrium, for use in a pacemaker system, comprising
    positioning a first floating whole-ring bipole in said patient's lower atrium near the tricuspid valve, and
    positioning a first floating split-ring bipole in said patient's upper attrium near the sinus node.

10. The method as described in claim 9, further comprising positioning the electrodes of said split-ring bipole diagonally.

11. The method of claim 9, wherein said split-ring bipole is positioned about 15 to 60 mm from said whole-ring bipole.

12. The lead as described in claim 9, further comprising positioning a second split-ring bipole and a second whole-ring bipole intermediate of said first floating whole-ring bipole and said first split-ring bipole.

13. A pacing system comprising a pacemaker having stimulus means for generating stimulus signals for delivery to a patient's ventricle and sense means for receiving signals sensed in the patient's atrium, in combination with a lead for use with said pacemaker, said lead having at about its proximal end a connector connecting said lead to said pacemaker, and a stimulus electrode at about its distal end for delivering said stimulus signals, at least first and second bipoles positioned on said lead for sensing signals in said atrium, and conducting means for conducting signals between said distal electrode and said connector and between said bipoles and said connector, the first of said bipoles comprising a pair of whole-ring electrode and the second of said bipoles comprising a pair of split-ring electrode.

* * * * *